United States Patent [19]

Kee

[11] Patent Number: 5,628,306
[45] Date of Patent: *May 13, 1997

[54] RESPIRATORY MANIFOLD WITH ACCESSORY ACCESS PORT

[76] Inventor: Kok-Hiong Kee, 2507 Barrett Place Dr., St. Louis, Mo. 63021

[*] Notice: The term of this patent shall not extend beyond the expiration date of Pat. No. 5,333,607.

[21] Appl. No.: 230,983

[22] Filed: Apr. 21, 1994

Related U.S. Application Data

[63] Continuation-in-part of Ser. No. 962,755, Oct. 19, 1992.

[51] Int. Cl.$^6$ .................................................. A61M 25/01
[52] U.S. Cl. ........................ 128/203.12; 128/207.16; 128/207.14; 604/266; 604/267; 604/268
[58] Field of Search ........................ 604/283, 284, 604/266–269, 905, 256, 249, 167; 128/207.14, 207.16, 203.12

[56] References Cited

U.S. PATENT DOCUMENTS

| | | | |
|---|---|---|---|
| 1,588,336 | 6/1926 | Richmond | 285/331 X |
| 3,416,567 | 12/1968 | Von Dardel et al. | 137/604 |
| 4,240,417 | 12/1980 | Holever | 128/203.12 |
| 4,346,702 | 8/1982 | Kubota | 128/207.14 |
| 4,351,328 | 9/1982 | Bodai | 128/202.16 |
| 4,426,062 | 1/1984 | Bowron | 251/7 |
| 4,510,933 | 4/1985 | Wendt | 128/207.14 |
| 4,569,344 | 2/1986 | Palmer | 128/207.16 |
| 4,781,702 | 11/1988 | Herrli | 604/244 |
| 4,805,611 | 2/1989 | Hodgkins | 128/207.14 |
| 4,836,199 | 6/1989 | Palmer | 128/207.16 |
| 4,850,350 | 7/1989 | Jackson | 128/207.16 |
| 4,857,062 | 8/1989 | Russell | 604/167 |
| 4,951,661 | 8/1990 | Sladek | 128/202.27 |
| 5,000,745 | 3/1991 | Guest et al. | 604/256 |
| 5,009,391 | 4/1991 | Steigerwald | 251/149.1 |
| 5,083,561 | 1/1992 | Russo | 128/207.16 |
| 5,114,408 | 5/1992 | Fleischhaker et al. | 604/256 |
| 5,154,701 | 10/1992 | Cheer et al. | 604/256 |
| 5,158,569 | 10/1992 | Strickland | 604/283 |
| 5,215,522 | 6/1993 | Page et al. | 604/33 |
| 5,333,607 | 8/1994 | Kee et al. | 128/207.14 |

*Primary Examiner*—Edgar S. Burr
*Assistant Examiner*—William J. Deane, Jr.
*Attorney, Agent, or Firm*—Montgomery W. Smith; Gene B. Kartchner; Ari M. Bai

[57] ABSTRACT

A ventilator manifold is disclosed which includes a port for attachment and detachment of an accessory device thereto without interruption of continuous respiratory support of the patient. A particular embodiment of an accessory device described herein includes a suctioning device for removal of fluids from a patient's lungs during respiratory support. The manifold includes an accessory access port which has a normally closed valve therein which remains closed regardless of the pressure changes within the manifold. The normally closed valve is positioned in the port such that insertion of an accessory device adaptor therein forces the normally closed valve to an open position. Removal of the adaptor of the accessory device allows the normally closed valve to return to its closed position, thus allowing continued operation of the respiratory system even when no accessory device is present in the accessory device access port.

5 Claims, 4 Drawing Sheets

RESPIRATORY MANIFOLD WITH ACCESSORY ACCESS PORT

This application is a continuation-in-part of U.S. patent application Ser. No. 07/962,755 filed Oct. 19, 1992 for "Ventilator Manifold with Accessory Access Port".

BACKGROUND OF THE INVENTION

1. Field of the Invention

This invention relates generally to apparatus used in conjunction with a respiratory support system. More specifically, the present invention relates to a method and apparatus for the attachment of accessory devices to a respiratory support system. Even more specifically, the present invention relates to a ventilator manifold for use with a respiratory support system which accommodates the attachment and detachment of accessory access devices therewith without interruption or loss of continuous respiratory support of a patient.

2. Prior Art

Respiratory support systems used for the ventilation of critically ill patients are now commonly used in medical facilities. Typically, a prior art respiratory support system includes a tracheal tube positioned either directly, or through the nose or mouth, into the trachea of a patient, a manifold connected to the tracheal tube at one port position thereof, and a source of breathable gas connected at a second port thereof. The purpose of the respiratory support system is to assist the patient in maintaining adequate blood oxygenation levels without overtaxing the patient's heart and lungs.

While a patient is attached to the respiratory support system, it is periodically necessary to aspirate fluid from the patient's trachea or lungs. In the past, in order to accomplish aspiration, it has been necessary to disassemble part of the respiratory support system, either by removing the ventilator manifold therefrom or by opening a port of the manifold and inserting a small diameter suction tube down the tracheal tube and into the patient's trachea and lungs. The fluid was then suctioned from the patient and the suction catheter was removed and the respiratory support system reassembled. However, due to the interruption of respiratory support during this procedure, a patient's blood oxygen often dropped to an unacceptably low level, even when other previously known breathing assistance efforts were simultaneously provided.

One solution to the above problem, which is generally exemplary of the prior art, is shown in U.S. Pat. No. 5,073,164 to Hollister et al., which includes a ventilator manifold having an access port therethrough which is adapted to receive a connector of the suction catheter device. The suction catheter device positions a catheter within the ventilator manifold without substantial manifold pressure loss. The suction catheter device includes an envelope which is positioned around the catheter portion thereof in order to prevent contamination of catheter surfaces intended to be inserted into the patient's trachea and lungs.

Although this type of ventilator manifold and suction catheter device connection allows continuous respiratory support of the patient during suctioning of fluid from the patient, it nevertheless has several drawbacks associated with its use. For example, removal of the suction catheter device from the manifold, such as for the purpose of replacing the suction catheter device, or for attaching another accessory to the manifold (e.g., a manual resuscitation bag or a metered dose inhaler) cannot be accomplished without loss of internal manifold pressure and thereby a compromise of the integrity of the respiratory system. Further, separation of Hollister et als'. suction catheter device from their suction control valve cannot be accomplished without opening the manifold to atmospheric pressure through the catheter. Therefore, replacement of either the suction catheter device or the suction control valve is not possible without loss of internal manifold pressure. Instead, respiratory support of the patient is compromised whenever the suction catheter device or the suction control valve is removed from the system for any reason. Since the suction catheter device tends to become contaminated relatively quickly with respect to the suction control valve and the ventilator manifold, it must be changed out of the system and replaced on a relatively frequent basis. However, because of the problems caused by loss of respiratory support during replacement, the ventilator manifold and/or the suction control valve are often prematurely discarded along with the suction catheter device in order to limit replacement time and the number of replacement procedures required.

U.S. Pat. No. 4,351,328 to Bodai attempts to solve one of the above problems by forming an opening in the ventilator manifold which is blocked by a pre-punctured resilient seal through which a catheter can be passed without substantially effecting the integrity of the system, i.e., without substantial gas exchange or pressure loss between the interior of the manifold and the atmosphere.

The Bodai device, although allowing entry and removal of a suction catheter through the ventilator manifold during continuous respiratory support of a patient, nevertheless fails to completely resolve the existing problems in the prior art. Specifically, the pre-punctured resilient material in Bodai's manifold opening allows only for the insertion of a catheter therethrough, and fails to accommodate a suction catheter device which includes a collapsible envelope which surrounds and seals the catheter against exterior surface contamination. Because of this, the suction catheter must be replaced after each use. Further, there is no design consideration for the attachment of other accessory devices to the manifold, such as a manual resuscitation bag or a metered dose inhaler, which are often necessary for use in the care of a patient.

Also, the system described by Bodai tends to cause mucus and other fluids from the patient's lungs and trachea to collect in the manifold as the catheter is pulled past the pre-punctured resilient seal when being withdrawn. Because of this contamination problem, it is often necessary to replace the manifold on a more frequent basis than would otherwise be necessary, which necessitates a pressure breach in the support system.

There therefore exists a need in the art for a respiratory support system which includes a ventilator manifold which allows simple attachment and detachment of an accessory access device therefrom during continuous patient respiratory support, without substantial pressure loss from the manifold and without substantial collection of body fluids in the manifold.

OBJECTS AND SUMMARY OF THE INVENTION

A principle object of the present invention is to provide a respiratory support system which allows attachment thereto and detachment therefrom of accessory devices, such as a suction catheter device, without interruption of continuous patient respiratory support.

Another object of the present invention is to provide a respiratory system which allows access of accessory devices thereto through an accessory access port within the manifold which is normally closed against the atmosphere and which will open upon attachment of the accessory device and automatically reclose upon detachment thereof.

A further object of the present invention is to provide a respiratory system having a manifold which includes an accessory device access port with a normally closed valve therein, which can accommodate an adaptor formed as part of the accessory device and which is designed to seal against the port and open the normally closed valve allowing interchangeable use of accessory devices within the manifold while maintaining manifold pressure integrity.

These and other objects of the present invention are realized in a presently preferred embodiment thereof, described by way of example and not necessarily by way of limitation, which provides for interchangeable use of accessory devices with a manifold of a ventilator system during respiratory support of a patient, without compromising the integrity of the system by causing significant pressure loss through the manifold. The invention includes a ventilator manifold formed with an accessory device access port which includes a normally closed valve therein. The valve maintains the pressure differential between the atmosphere and the interior of the manifold regardless of manifold pressure fluctuations. The accessory device access port also includes a sleeve member positioned within the port which lines the port interior surface and assists in sealing against an adaptor of the accessory device as it is inserted into the port. The sleeve member also passes through a side opening in the port and attaches to a pigtail type fluid injection tube which is adapted for allowing injection of fluid therethrough into the access port and through the sleeve member into the adaptor for cleaning purposes. The pigtail may include a one-way valve for preventing retrograde movement of fluid therethrough.

The invention may also include an adaptor which is formed to fit within the accessory device access port and sealingly engage with the sleeve member and the normally closed valve. Positioning the adaptor into the access port forces the normally closed valve to an open position. The access port and adaptor include a detent and stop-type locking mechanism for locking the adaptor within the port against inadvertent withdraw thereof during use, and for properly orienting the adaptor within the port to form a clear passage through the port and adaptor for the insertion and removal of a medical instrument. The adaptor includes a side opening therein which is orientable relative to the stop-type locking mechanism to cause it to align with the side opening of the sleeve member and the access port when the adaptor is properly positioned within the access port and locked in place for use.

The adaptor may be formed as part of, or for use with, any one of a number of common respiratory support system accessories, such as a suction catheter device, a metered dose inhaler, a manual resuscitation bag, a bronchoscope or the like.

In the presently shown preferred embodiment of the invention, the adaptor is part of a suction catheter device, and may include a seal through which the suction catheter thereof is inserted for extension through the manifold into the patient's trachea and lungs. The adaptor seal is designed to ensure that the internal pressure in the manifold is not lost through the adaptor, and that the cleaning fluid injected through the pigtail tube, which passes through the access port into the adaptor, will be effective in cleaning the suction catheter and will be entirely removed from within the adaptor interior by suctioning through the suction catheter after it has performed its desired cleaning function and will not be allowed to accumulate.

These and other objects and advantages of the present invention will become apparent from the following more detailed description, when taken in conjunction with the accompany drawings, in which like elements are identified with like numerals throughout.

DETAILED DESCRIPTION OF THE PREFERRED EMBODIMENTS

Figure 1:
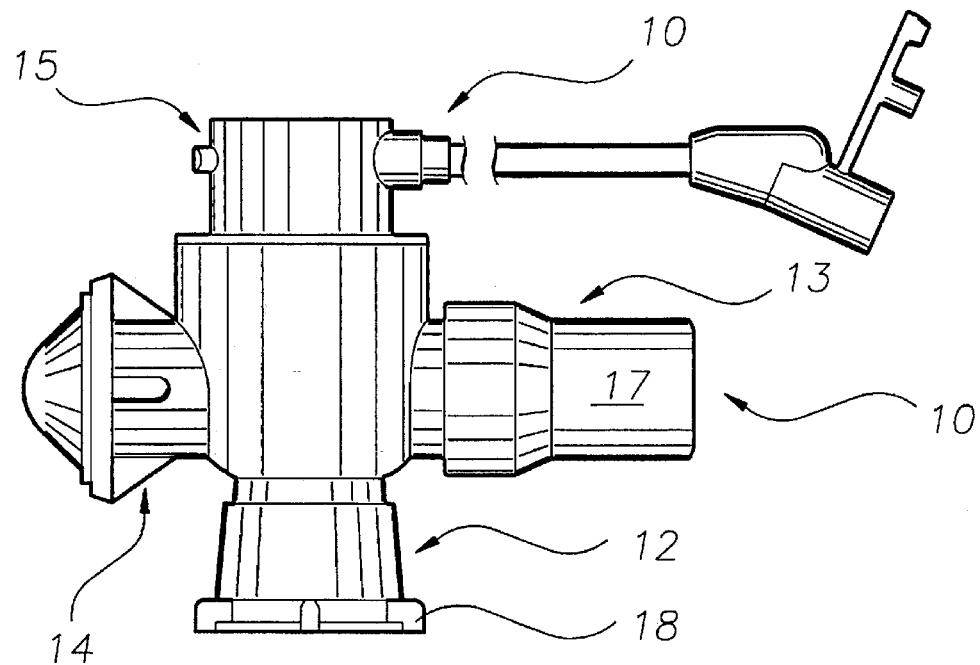
FIG. 1 shows a ventilator manifold of a respiratory support system which has been modified to include an accessory device access port formed in accordance with the principles of the present invention.

As shown in the exemplary drawings for the purposes of illustration, an embodiment of a ventilator manifold made in accordance with the principles of the present invention, referred to generally by the reference numeral 10, is provided for interchangeable access of respiratory system accessory devices. Also shown for purposes of illustration is an embodiment of an adaptor 11, formed as part of a suction catheter device, which is provided for air-tight attachment to the manifold 10.

As shown in FIG. 1, the ventilator manifold 10 of the present invention includes a plurality of access ports which facilitate its connection to a patient and to a ventilator circuit of a respiratory support system. The manifold 10 is attached to a patient for fluid flow communication with the patient's lungs by the connection of the patient attachment port 12 thereof to the connector of an endotracheal tube assembly (not shown) which has been previously positioned in the trachea of a patient by any one of several well known procedures.

The weaning port 14 is normally kept covered by a cap, and the ventilator circuit connection port 13 of the manifold 10 is connected to flexible breathing hoses from the respiratory support system (not shown) in a well known manner, such as through a "Y" site connector.

The ventilator circuit connection port 13 and the patient attachment port 12 may, if desired, include swivel connectors 17 and 18 respectively thereon in order to allow relative rotation between the manifold 10 and the trachea tube and breathing hoses in order to isolate the trachea tube from incidental forces exerted thereon by the manifold 10 or the breathing hoses attached thereto so as to increase the comfort of the patient.

The ventilator circuit attached to port 13 provides an oxygen mixture to the patient and receives the expelled air from the patient. The ventilator circuit commonly includes various valves, regulators and the like associated with the hoses attached to the port 13 to effect respiration of the patient. The manifold 10, and hoses attached thereto at the ventilator circuit connection port 13, are generally made of disposable plastic material and are generally intended to be used by only one patient and then discarded.

When attached to the patient, the entire respiratory support system is designed to isolate the patient's lungs from the atmosphere and allow pressurized forced ventilation of a gas mixture of a high oxygen content from the ventilator into the patient's lungs. Commonly, respiratory support systems of this type employ a positive end expiratory pressure (PEEP) within the manifold 10 and the patient's lungs at all times during exhalation. This technique is used because of its benefit of ensuring that a minimum concentration of oxygen is supplied to the patient to maintain proper blood oxygenation levels. The PEEP procedure also keeps a large number of lung alveoli of the patient open at all times during respiratory support, thus increasing the effective lung area subject to ventilation.

Prevailing respiratory support techniques, including PEEP, have made it very disadvantageous to interrupt respiratory support to the patient by opening the ventilator manifold 10 to the atmosphere. Therefore, the necessary attachment and detachment of accessory devices such as a suction catheter device or the like for medical procedures has been difficult due to the loss of isolation of the respiratory system from the atmosphere during these procedures, and the immediate loss of effective lung surface area due to alveoli collapse. Further, when such procedures have been prolonged for any reason, the patient's blood oxygen has often dropped to inadequate levels, and subsequently forced overexertion of the patient's lungs and heart in order to return the blood oxygenation level to normal. Also, disassembly and reassembly of the respiratory system for procedures with prior art accessory devices has in the past been very time consuming for the medical worker.

The present invention resolves the problems associated with loss of isolation of the respiratory system from the atmosphere (i.e loss of PEEP) when various accessory devices must be attached or detached for use in performing necessary medical procedures during respiratory support.

Specifically, the manifold 10 of the present invention includes an accessory device access port 15 which is in fluid flow communication with the interior of the manifold 10 and the atmosphere and can be accessed without loss of PEEP.

Figure 2:
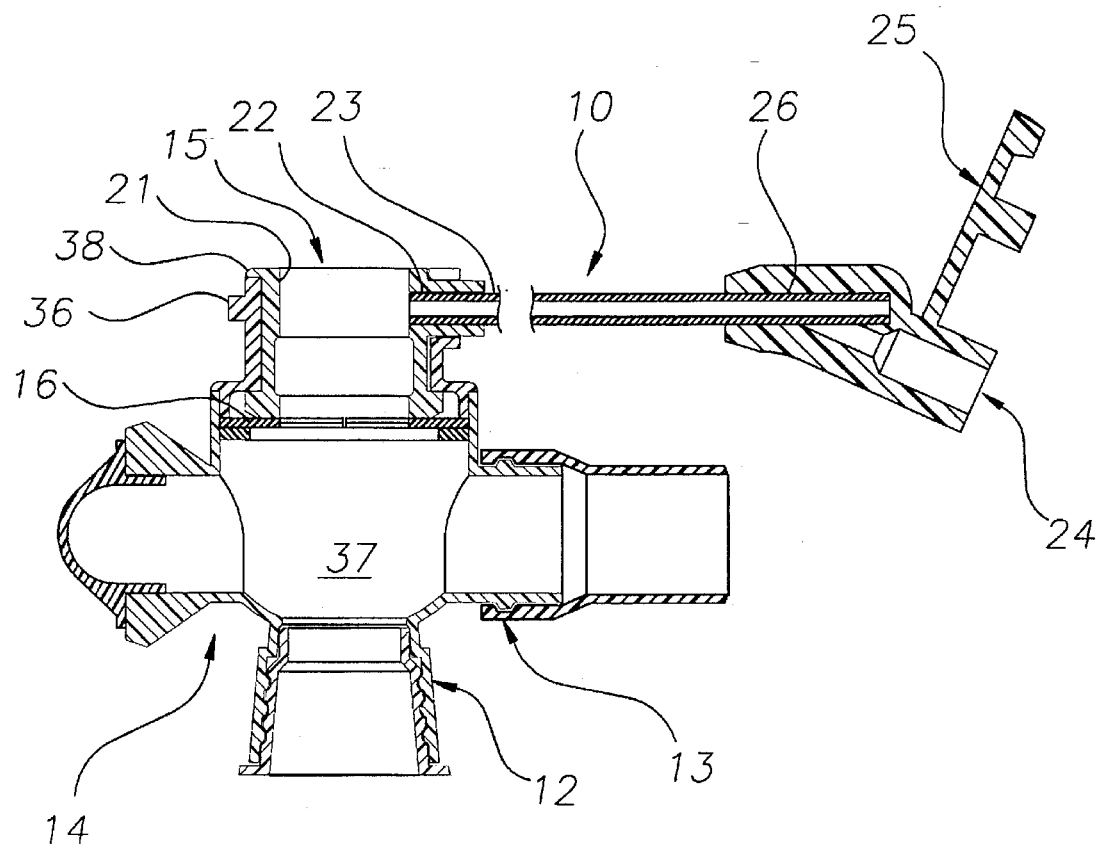
FIG. 2 shows a cross-sectional view of the ventilator manifold of FIG. 1.

As best shown in FIG. 2, the access port 15 includes a normally closed valve 16 formed therein which maintains the interior of the manifold 10 isolated from the atmosphere at all times. As explained above, the interior of the manifold 10, although experiencing constant pressure fluctuations, is generally kept at a pressure which is slightly above atmospheric pressure in order to properly administer oxygen according to the PEEP procedure. Therefore, the valve 16 is preferably made of a resilient material to ensure that pressure isolation of the manifold 10 is maintained. The valve 16 is preferably formed to a circular disk shape and inserted into the manifold 10 between the access port 15 and a support ring 19.

Figure 3:
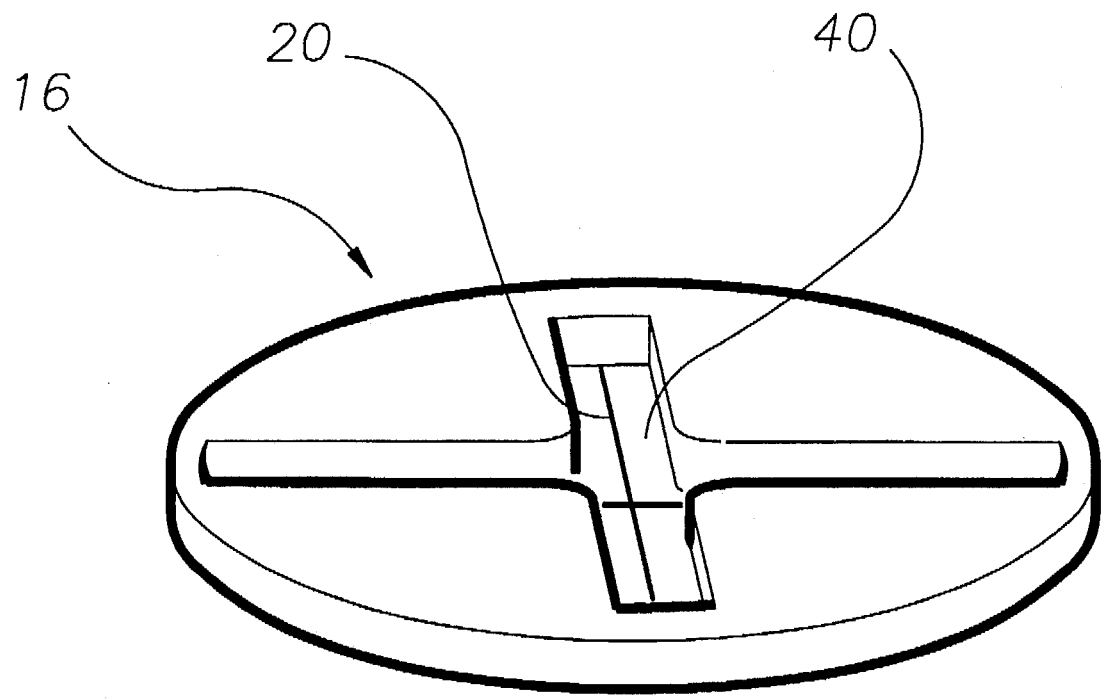
FIG. 3 is an isometric view of the normally closed valve of the present invention.
Figure 5:
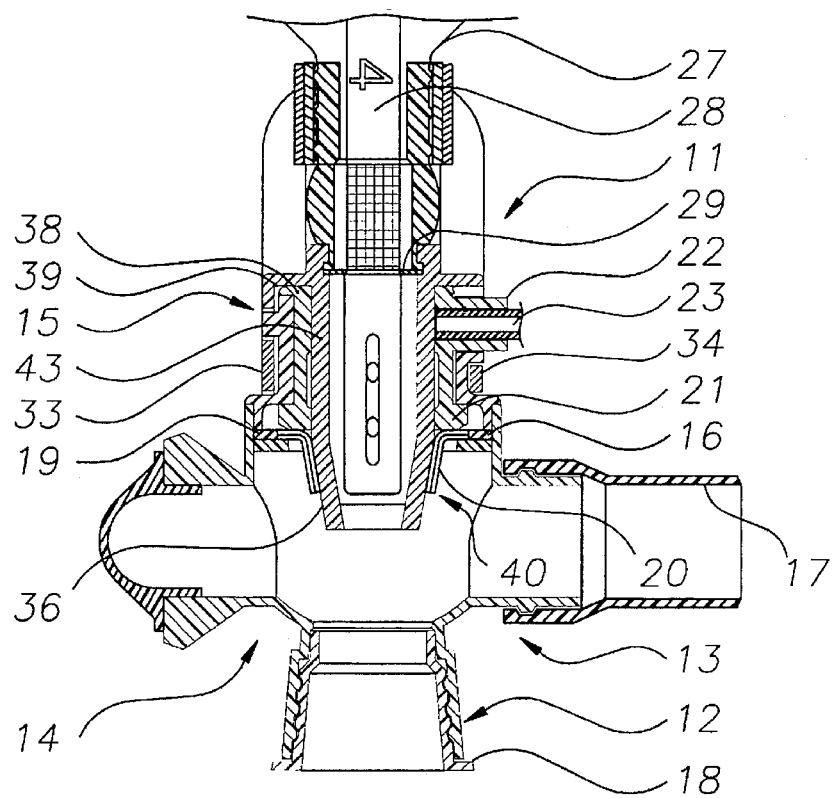
FIG. 5 is a cross-sectional view of the ventilator manifold with the adaptor attached thereto.

As shown in FIGS. 2 and 3, the valve 16 is formed with a slit, or a pair of perpendicular slits 20 which are normally closed against fluid flow therethrough, but may be forced opened by the insertion of the adaptor 11 completely into the access port 15 (see FIG. 5). The perpendicular slits 20 are adjacent a reduced thickness portion 40 of the valve 16 which operates to ensure that reclosure of the valve 16 after withdrawal of the adaptor 11 is complete and airtight, and avoids the possibility of incomplete closure due to overlapping of sections of the valve adjacent the slits 20. The reduced thickness portion 40 ensures that the slits 20 return to an adjacent abutting position upon withdrawal of the adaptor 11.

The interior of the access port 15 is lined with a sleeve member 21 which covers the entire interior surface of the access port 15 and abuts in sealing relationship against the normally closed valve 16. The interior diameter of the sleeve member 21 is predetermined to cause a snug fit with the adaptor 11 (as best shown in FIG. 5) to assist in the prevention of leakage from the manifold 10 when the normally closed valve 16 is forced opened by the adaptor 11.

The access port 15 forms a side opening 22 through which a portion of the sleeve 21 extends to be attached, such as by solvent bonding, to a pigtail fluid injection tube 23 which is intended for use in transporting fluid through the access port side opening 22 into the interior of the access port 15. The opposite end of the pigtail tube 23 includes a luer connector 24 attached thereto with an integrally formed luer connector plug 25. A check valve 26, taking the form of a collapsible sleeve, is positioned between the luer connector 24 and the pigtail tube 23 and collapses upon injection of fluid through the luer connector 24 into the pigtail tube 23, but expands to block fluid flow in the opposite direction.

It is preferred that the sleeve member 21 be formed of a relatively flexible material such as plasticized PVC, having good solvent bonding characteristics with the material forming the pigtail tube 23, the pigtail tube 23 preferably being formed of the same material as the sleeve member 21. The access port 15 according to the preferred embodiment of the present invention is preferably formed of clear plastic, which is preferably the same material forming the main body of the manifold 10 in order to ensure good ultrasonic or solvent bonding therebetween.

Figure 4:
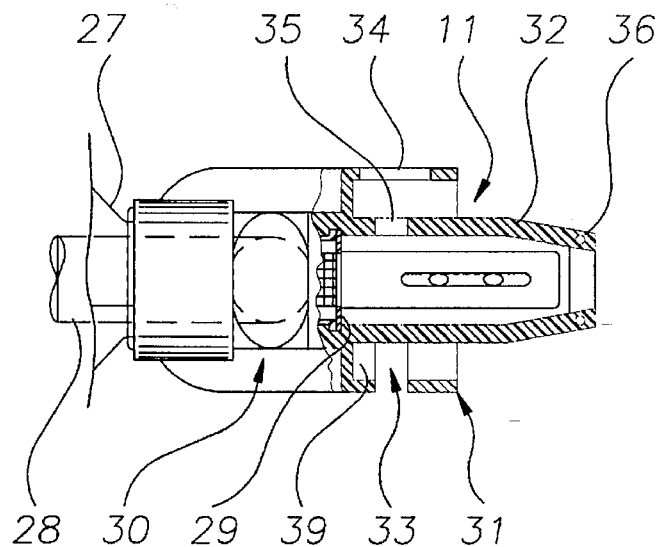
FIG. 4 is a partial cutaway view of a portion of an accessory device which includes an adaptor formed in accordance with the principles of the present invention.

In FIG. 4, a partial cross-sectional view of the adaptor 11 of the present invention as attached to an accessory device is shown. The accessory device (shown only in part) in the preferred embodiment of the invention is a suction catheter device. The adaptor 11 is permanently attached to the distal end of a sheath 27 which is designed to isolate the suction catheter 28 from direct contact with the user. Further, in the present embodiment, the adaptor 11 preferably includes a sealing ring 29 formed in the housing 30 thereof through which the suction catheter 28 must pass in order to pass through the adaptor 11 and into the manifold 10 during use. The seal ring 29 is designed to allow movement of the suction catheter 28 therethrough while at the same time maintain a seal thereabout.

A locking cylinder 31 may be formed to encircle a portion of the adaptor insertion member 32 and includes a pair of arcuate slots 33 and 34 which operate together as a locking mechanism to ensure secure attachment of the adaptor 11 to the access port 15 of the manifold 10, and also ensures proper relative orientation therebetween to cause the insertion member opening 35 of the adaptor 11 to be positioned in alignment with the side opening 22 of the access port 15 when the adaptor 11 is properly locked in position therein for use.

As can be seen in FIG. 4, the arcuate slot 33 is sized to be engageable with the nub 36 which is located directly opposite the side opening 22 on the access port 15. The arcuate slot 34 is larger in width than the arcuate slot 33 and therefore can accommodate the side opening 22 of the access port 15. As is readily evident, since the arcuate slots 33 and 34 are sized differently to accommodate the nub 36 and the side opening 22 respectively, of the access port 15, the adaptor 11 can only be locked in position within the access port 15 in one unique relative orientation therewith in which the insertion member opening 35 and the side opening 22 are in alignment.

As best shown in FIG. 5, attachment of the adaptor 11 to the respiratory manifold 10 is effected by insertion of the adaptor 11 into the access port 15 until the tapered top section 36 of the insertion member 32 engages the valve 16 and forces it toward the interior of the manifold 10. Upon complete insertion of the adaptor 11 into the port 15, the valve 16 is completely open and the sleeve member 21 is sealingly engaged with the insertion member 32. Also, the sleeve shoulder 38 of the sleeve member 21 is forced to resiliently deform within the base 39 of the locking cylinder 31. This increases the air tight seal and assists in positively locking the adaptor 11 to the access port 15 by forcing the arcuate slots 33 and 34 against the nub 36 and side opening 22 respectively.

It is intended that during insertion of the adaptor 11 into the access port 15, the sealing relationship formed between the sleeve member 21 and the insertion member 32 commence prior to opening of the valve 16 by the tapered top section 36, in order to ensure isolation of the interior of the manifold 10 from the atmosphere during attachment of the accessory device. Once completely inserted within the port 15, the tapered top section 36 extends completely through the access port 15 and into the manifold central chamber 37.

As shown in FIG. 5, the pigtail tube 23 can be used to inject fluid into the adaptor 11 to clean the suction catheter 28 and the sealing ring 29 of mucal materials which may have accumulated therein due to repeated insertion and withdrawn of the catheter 28 from the patient's lungs during aspiration procedures. The cleaning fluid can then be aspirated through the catheter 28 to remove it from the interior of the adaptor 11.

Figure 7:
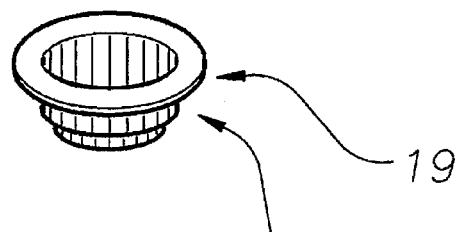
FIG. 7 is a perspective view of the second preferred embodiment of the seal support of the present invention.
Figure 6:
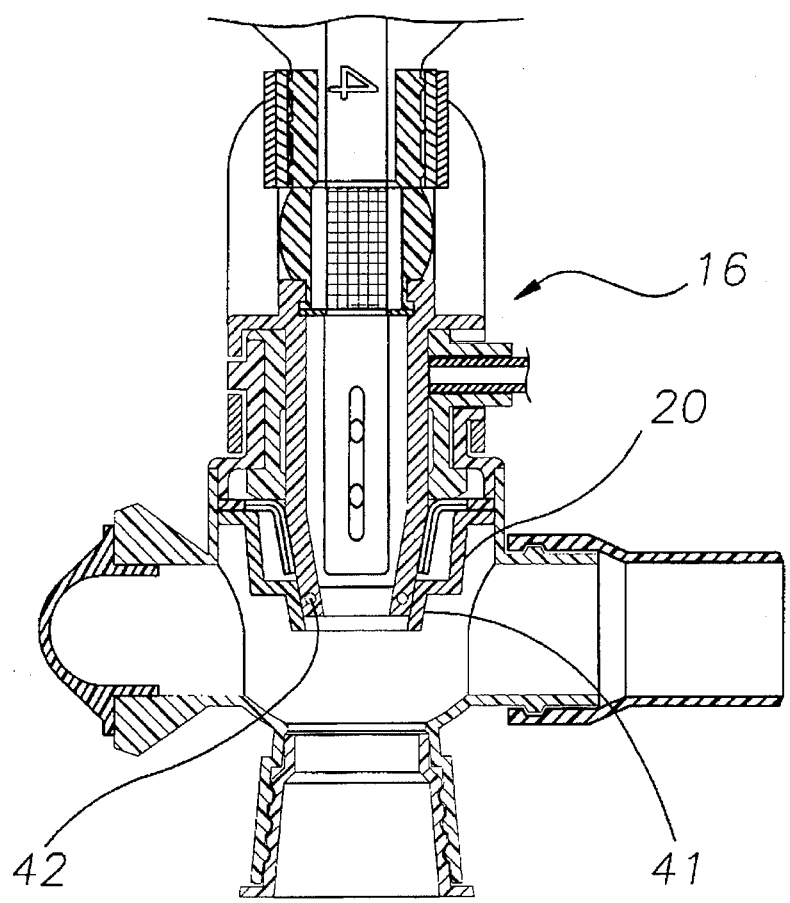
FIG. 6 is a cross-sectional view of a second preferred embodiment of a ventilator manifold made in accordance with the principles of the present invention.

FIGS. 6 and 7 show a second preferred embodiment of the present invention. This embodiment is identical to the first preferred embodiment explained above except that the support ring 19 thereof has been modified to include a redundant seal 41 which is sized to receive the tapered top section 36 of the adaptor 11 in a fluid sealing relationship.

If desired, the tapered top section 36 of the adaptor 11 may also include an O-ring 42 which is sized to match the diameter of the opening in the redundant seal 41 and which is positioned to be located in abutting and sealing relationship with the redundant seal 41 when the adaptor 11 is positioned completely within the access port 15.

When it is desired to remove the accessory device from the manifold 10, it is only necessary to unlock the adaptor 11 from the slots 33 and 34 of the access port 15, and withdraw the adaptor 11 therefrom. Due to the resilient nature of the valve 16, upon withdrawal of the adaptor 11 it will return to its normally closed position without exposure of the interior of the manifold 10 to the atmosphere. In this manner, accessory devices may be attached and detached periodically to the manifold 10 without interruption of continuous respiratory support of a patient by the respiratory support system and without loss of isolation of the respiratory support system from the atmosphere.

It should be understood from the foregoing that, while particular embodiments of the invention have been illustrated and described, various modifications can be made thereto for their adaptation to various accessory devices which require access to a patient's lungs while maintaining isolation of the respiratory support system from the atmosphere. It is to be understood that adaptation of the present invention for use on any such accessory device is intended to be well within the spirit and scope of the present invention.

Although particular embodiments of the invention have been shown, it is not intended that the invention be limited thereby, instead, the scope of the present invention is intended to be limited only by the appended claims.

I claim:

1. A respiratory support system comprising:

an adaptor formed as part of a respiratory system accessory device, a catheter housed within said adaptor, a manifold adapted to be connected for fluid flow attachment between a patient and a ventilator circuit, said manifold having an accessory access port for allowing attachment of said adaptor to said manifold, said accessory access port including a normally closed valve therein and a normally open redundant sealing member, and said adaptor including means for opening said normally closed valve in response to attachment of said adaptor to said accessory access port to allow fluid flow access between said manifold and said respiratory system accessory device, said adaptor further including means for abutting against said normally open redundant sealing member to seal thereagainst, whereby said catheter maybe introduced into said manifold without contact with possible contamination by said normally closed valve.

2. A respiratory support system according to claim 1 wherein said normally closed valve includes a slit valve having at least one slit therein in which said slit forms adjacent surfaces which abut each other in a normally closed position for sealing said normally closed valve, and which are separated by said adaptor when said adaptor operates to open said normally closed valve.

3. A respiratory support system according to claim 2 wherein said slit valve includes reduced thickness portions which are located directly adjacent said at least one slit.

4. A respiratory support system comprising:

an adaptor formed as part of a respiratory system accessory device, a catheter housed within said adaptor, a manifold adapted to be connected for fluid flow attachment between a patient and a ventilator circuit, said manifold having an accessory access port for allowing attachment of said adaptor to said manifold, said accessory access port including a normally closed valve therein which includes a slit valve having at least one slit therein, said at least one slit forming adjacent surfaces which abut each other when said normally closed valve is in a normally closed position, said slit valve further including a reduced thickness portion located directly adjacent said at least one slit, said reduced thickness portion assisting said adjacent surfaces at returning to their abutting position during reclosure of the normally closed valve, said adaptor including a means for opening said normally closed valve in response to attachment of said adaptor to said accessory access port to allow fluid flow access between said manifold and said respiratory system accessory device, whereby said catheter maybe introduced into said manifold without contact with possible contamination by said normally closed valve.

5. A respiratory support system according to claim 4 wherein said accessory access port further includes a normally open redundant sealing member and said adaptor includes means for abutting against said normally open redundant sealing member to seal thereagainst.

* * * * *